(12) United States Patent
Kimura

(10) Patent No.: US 8,873,709 B2
(45) Date of Patent: Oct. 28, 2014

(54) RADIOGRAPHIC IMAGING SYSTEM AND RADIOGRAPHIC IMAGING METHOD

(75) Inventor: Youichi Kimura, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 404 days.

(21) Appl. No.: 13/367,513

(22) Filed: Feb. 7, 2012

(65) Prior Publication Data

US 2012/0201354 A1    Aug. 9, 2012

(30) Foreign Application Priority Data

Feb. 7, 2011    (JP) ................................. 2011-024147

(51) Int. Cl.
*A61B 6/00*    (2006.01)
*A61B 6/04*    (2006.01)

(52) U.S. Cl.
CPC ............. *A61B 6/5235* (2013.01); *A61B 6/4429* (2013.01); *A61B 6/505* (2013.01); *A61B 6/589* (2013.01)
USPC ............ 378/62; 378/165; 378/166; 378/196; 378/197; 378/209

(58) Field of Classification Search
CPC .. A61B 6/4429; A61B 6/4452; A61B 6/4458; A61B 6/4464; A61B 6/447; A61B 6/4476; A61B 6/04; A61B 6/0407
USPC ................... 378/62, 165, 166, 196, 197, 209
See application file for complete search history.

(56) References Cited

U.S. PATENT DOCUMENTS

| | | | |
|---|---|---|---|
| 6,463,121 B1 * | 10/2002 | Milnes | 378/62 |
| 6,895,076 B2 * | 5/2005 | Halsmer et al. | 378/98.12 |
| 6,934,362 B2 * | 8/2005 | Scheuering | 378/108 |
| 6,940,948 B1 * | 9/2005 | Tretiakov et al. | 378/146 |
| 6,944,265 B2 * | 9/2005 | Warp et al. | 378/98.12 |
| 7,054,412 B2 * | 5/2006 | Scheuering | 378/108 |
| 7,073,939 B2 * | 7/2006 | Spahn | 378/196 |
| 7,110,497 B2 * | 9/2006 | Halsmer et al. | 378/98.12 |
| 7,114,849 B2 * | 10/2006 | Atzinger et al. | 378/206 |
| 7,142,632 B2 * | 11/2006 | Atzinger et al. | 378/62 |
| 7,522,701 B2 * | 4/2009 | Jensen et al. | 378/62 |
| 7,555,100 B2 * | 6/2009 | Wang et al. | 378/98.12 |
| 7,556,427 B2 * | 7/2009 | Yu et al. | 378/196 |
| 7,593,555 B2 * | 9/2009 | Spahn | 382/128 |
| 7,684,605 B2 * | 3/2010 | Klingenbeck-Regn | 382/132 |
| 7,708,462 B2 * | 5/2010 | Fujiwara et al. | 378/207 |

(Continued)

FOREIGN PATENT DOCUMENTS

| | | | | |
|---|---|---|---|---|
| JP | 2004-0568 A | 1/2004 | | |
| JP | 2009-240681 A | 10/2009 | | |
| JP | 2010-94498 A | * 4/2010 | ............... | A61B 6/00 |

*Primary Examiner* — Allen C. Ho
(74) *Attorney, Agent, or Firm* — Jean C. Edwards; Edwards Neils PLLC

(57) ABSTRACT

A radiographic imaging system is capturing a radiographic image of a subject. The radiographic imaging system has a radiation detector that detects radiation from which the radiographic image is obtained, a radiation source that irradiates the radiation detector with the radiation, a partition that is disposed adjacent to the radiation detector and that locates the subject at a predetermined position relative to the radiation detector, a distance measuring unit that measures a distance between the partition and the radiation source, a tilt detecting unit that measures a tilt of the partition, and an image processor that corrects the captured radiographic image based on the distance between the partition and the radiation source obtained by the distance measuring unit and the tilt of the partition obtained by the tilt detection unit.

16 Claims, 4 Drawing Sheets

(56) References Cited

U.S. PATENT DOCUMENTS

| | | | |
|---|---|---|---|
| 7,953,206 B2* | 5/2011 | Oogami | 378/98.12 |
| 8,064,572 B2* | 11/2011 | Sato | 378/62 |
| 8,084,744 B2* | 12/2011 | Enomoto | 250/370.09 |
| 8,160,205 B2* | 4/2012 | Saracen et al. | 378/69 |
| 8,201,999 B2* | 6/2012 | Uchida et al. | 378/197 |
| 8,275,187 B2* | 9/2012 | Oogami | 382/131 |
| 8,300,764 B2* | 10/2012 | Yamaguchi | 378/62 |
| 8,344,327 B2* | 1/2013 | Yamaguchi | 250/363.07 |
| 8,351,568 B2* | 1/2013 | Minnigh et al. | 378/62 |
| 8,360,639 B2* | 1/2013 | Kato | 378/197 |
| 8,433,038 B2* | 4/2013 | Zeng | 378/97 |
| 8,529,128 B2* | 9/2013 | Horiuchi | 378/197 |
| 2003/0215051 A1 | 11/2003 | Suzuki | |
| 2009/0245464 A1 | 10/2009 | Yamaguchi | |

\* cited by examiner

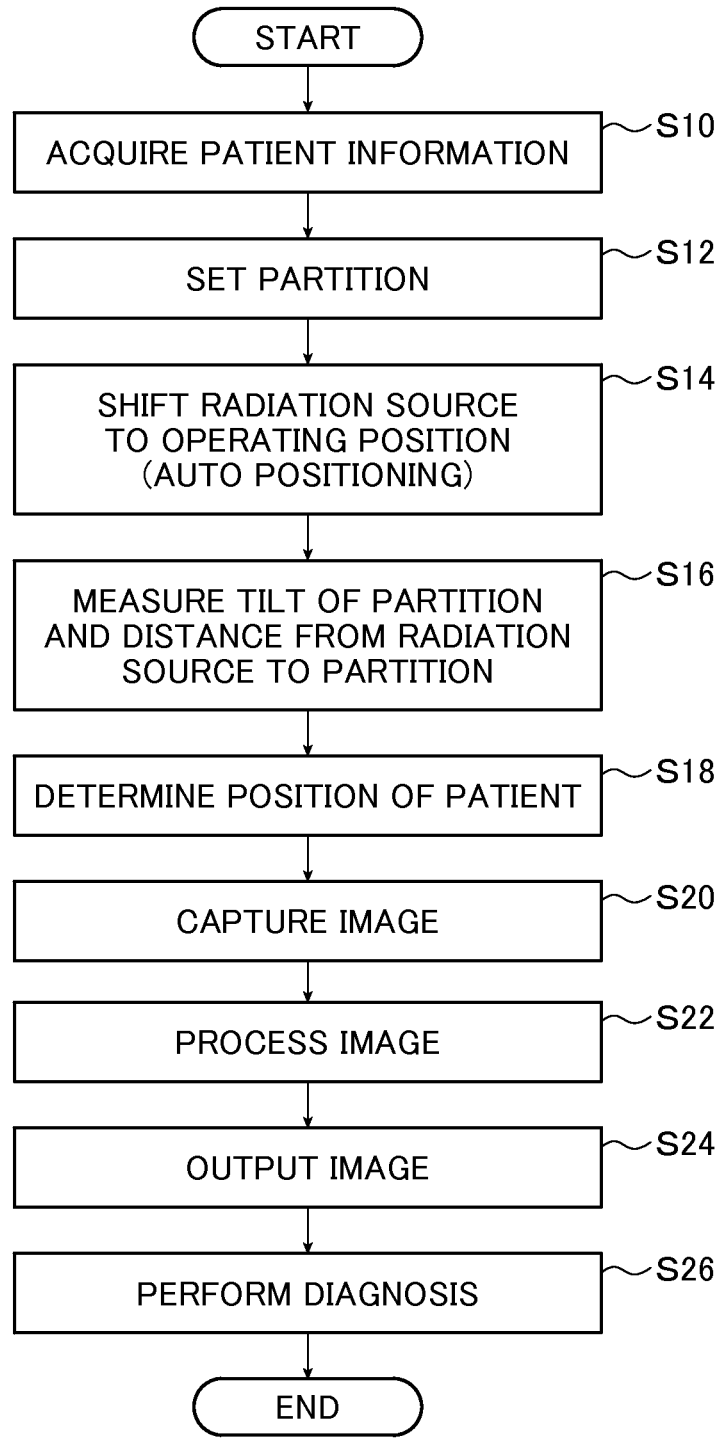

RADIOGRAPHIC IMAGING SYSTEM AND RADIOGRAPHIC IMAGING METHOD

CROSS-REFERENCE TO RELATED APPLICATIONS

The present application claims priority from Japanese Patent Application No. 2011-024147, filed on Feb. 7, 2011, the contents of which are herein incorporated by reference in their entirety.

BACKGROUND OF THE INVENTION

This invention relates to a radiographic imaging system and a radiographic imaging method that can image a subject such as an examinee or a patient with an upright position by the use of a partition, and more particularly, to a radiographic imaging system and a radiographic imaging method that can obtain an appropriate image even when a partition is tilted when imaging a subject with an upright position by the use of the partition.

Recently, radiographic imaging systems have been used in various fields such as medical diagnostic images or industrial nondestructive inspections. In some radiographic imaging systems, a flat panel detector (hereinafter, referred to as an FPD) converting radiation into an electrical signal is used as a radiation detector detecting radiation such as X-rays, $\alpha$ rays, $\beta$ rays, $\gamma$ rays, electron beams, or ultraviolet rays transmitted through a subject.

In the radiographic imaging systems employing the FPD, a subject is irradiated with radiation from a radiation source, the radiation transmitted through the subject is converted into electrical signals by the FPD, and the electrical signals corresponding to image data of the subject are read from the FPD to generate a radiographic image.

For example, the FPD is classified into two schemes of a direct scheme of collecting electron-hole pairs emitted from a photoconductive film in response to incidence of radiation and reading electrical signals, that is, directly converting the radiation into the electrical signals, and an indirect scheme of including a fluorescent layer (scintillator layer) formed of a fluorescent substance emitting light (fluorescing) in response to incidence of radiation, converting the radiation into visible rays through the use of the fluorescent layer, and reading the visible rays through the use of a photoelectric conversion device, that is, converting the radiations into the electrical signals via the visible rays. The photoconductive film is formed of amorphous selenium or the like.

Currently, the FPDs generally only have a size of about 43×43 cm. Accordingly, a long-area radiographic image such as a radiographic image of the whole area of a spine (whole spine) or the whole area of legs (whole legs) cannot be captured by a single imaging.

In the radiographic imaging system according to the related art capturing a radiographic image of a long area of the whole area of a spine (whole spine) or the whole area of legs (whole legs) by the use of the FPD, a partition is disposed between a patient and the FPD supported by an upright stand so as to achieve safe protection and to capture an image up to the heels when operating long length radiography. The patient is made to stand upright at a predetermined position by the partition, the imaging is performed while causing the FPD to sequentially move from above, and plural captured images are joined and synthesized into a long image (see JP 2009-240681 A).

SUMMARY OF THE INVENTION

As described above, the partition is disposed, the FPD is made to move, and a long area is imaged, whereby a long image is obtained. The long image is used for a diagnosis by measuring the distance of a region of interest or the like. Accordingly, when a large difference is present between an actual size and an image size, an erroneous diagnosis may result. For example, when a floor of a radiographic room is not flat but uneven, the partition may be tilted or the partition may depart from a predetermined position relative to the FPD. Accordingly, when a patient is made to stand at a predetermined position by the use of the partition, the distance between the patient and the FPD may vary or the patient's body axis may be tilted about the FPD. Therefore, it is necessary to raise the positional precision of the partition and the upright stand. Accordingly, for example, like the X-ray imaging apparatus disclosed in JP 2004-0568 A, the radiographic imaging system is known which corrects an obtained image by detecting a blur of a subject.

However, in the radiographic imaging system detecting a blur of a subject like the X-ray imaging apparatus disclosed in JP 2004-0568 A, there is a problem in that the system configuration is complicated. In addition, since it is necessary to detect the blur of a subject, there is also a problem in that imaging processes are troublesome.

In this way, in the radiographic imaging system in which a partition is disposed to image a long area, there is presently no way to raise the positional precision of the partition causing a patient to stand at a predetermined position and the upright stand.

An object of the present invention is to solve the problems in the aforementioned prior art, and to provide a radiographic imaging system and a radiographic imaging method that can obtain an appropriate image even when a partition is tilted when imaging a subject with an upright position by the use of the partition.

To achieve the above objectives, a first aspect of the present invention provides a radiographic imaging system capturing a radiographic image of a subject, comprising a radiation detector that detects radiation from which the radiographic image is obtained a radiation source that irradiates the radiation detector with the radiation a partition that is disposed adjacent to the radiation detector and that locates the subject at a predetermined position relative to the radiation detector a distance measuring unit that measures a distance between the partition and the radiation source a tilt detecting unit that measures a tilt of the partition and an image processor that corrects the captured radiographic image based on the distance between the partition and the radiation source obtained by the distance measuring unit and the tilt of the partition obtained by the tilt detection unit.

It is preferred that the measurement of the tilt of the partition by the tilt detecting unit and the measurement of the distance by the distance measuring unit are performed before or after capturing the radiographic image. Further, it is preferred that the measurement of the tilt of the partition by the tilt detecting unit is performed during capturing the radiographic image and the image processor corrects the captured radiographic image based on the tilt of the partition detected during capturing the radiographic image and the distance between the partition and the radiation source.

It is preferred that further comprising a detector moving unit that causes the radiation detector to move in the length direction of the subject, wherein the image processor synthesizes a plurality of images, which are obtained by causing the radiation detector to move in the length direction of the subject through the use of the detector moving unit, irradiating the subject with radiation from the radiation source, and capturing the images of the subject divided in the length direction, and creates a long radiographic image.

In this case, two subsequent imaging positions are made to partially overlap with each other when capturing the images of the subject divided in the length direction and the image processor matches the overlapping portions to enable the long radiographic image to be created.

A second aspect of the present invention provides a radiographic imaging method of capturing a radiographic image of a subject by the use of a radiation detector, a partition that locates the subject at a predetermined position relative to the radiation detector, and a radiation source that irradiates the radiation detector with radiation, the radiographic imaging method comprising the steps of measuring a distance between the partition and the radiation source and a tilt of the partition, capturing the radiographic image of the subject, and correcting the captured radiographic image based on the distance between the partition and the radiation source and the tilt of the partition.

A third aspect of the present invention provides a radiographic imaging method of capturing a radiographic image of a subject by the use of a radiation detector, a partition that locates the subject at a predetermined position relative to the radiation detector, and a radiation source that irradiates the radiation detector with radiation, the radiographic imaging method comprising the steps of capturing the radiographic image of the subject, measuring a distance between the partition and the radiation source and a tilt of the partition, and correcting the captured radiographic image based on the distance between the partition and the radiation source and the tilt of the partition.

It is preferred that a second measurement of the tilt of the partition is performed in the capturing of the radiographic image of the subject, and wherein the tilt of the partition obtained through the second measurement is used to correct the radiographic image in the step of correcting the captured radiographic image.

It is preferred that the step of capturing the radiographic image of the subject includes a step of causing the radiation detector to move in the length direction of the subject, irradiating the subject with the radiation from the radiation source, and capturing a plurality of images of the subject divided in the length direction, and a step of synthesizing the plurality of images obtained by imaging the subject divided in the length direction to create a long radiographic image.

It is preferred that when capturing the images of the subject divided in the length direction, two subsequent imaging positions are made to partially overlap with each other to image the subject divided in the length direction and the overlapping portions are matched with each other to enable the long radiographic image to be created.

According to the present invention, even when the partition is tilted when locating a subject at a predetermined position by the use of the partition and imaging the subject with an upright position, it is possible to correct a captured image based on the tilt. In addition, since the distance between the partition and the radiation source can be measured, there is no trapezoidal distortion or the like and the shift in enlargement ratio can be corrected, whereby it is possible to obtain an image of the subject having a small error in relation to the actual size. Accordingly, regarding a long radiographic image of the subject obtained by synthesizing plural images, there is no trapezoidal distortion and the error in relation to the actual size can be reduced. As a result, it is possible to improve diagnosis precision.

Since it is possible to correct a captured image based on the tilt of the partition, it is not necessary to adjust the position of the partition and to adjust the tilt of the partition. Accordingly, it is possible to facilitate the installation of the partition and to simplify the configuration of the partition.

BRIEF DESCRIPTION OF THE DRAWINGS

FIG. 4 is a flowchart illustrating a method of imaging a long area with the radiographic imaging system according to the first embodiment of the present invention.

DETAILED DESCRIPTION OF THE INVENTION

Hereinafter, a radiographic imaging system and a radiographic imaging method according to the present invention will be described in detail with reference to the preferred embodiments shown in the accompanying drawings.

Figure 1:
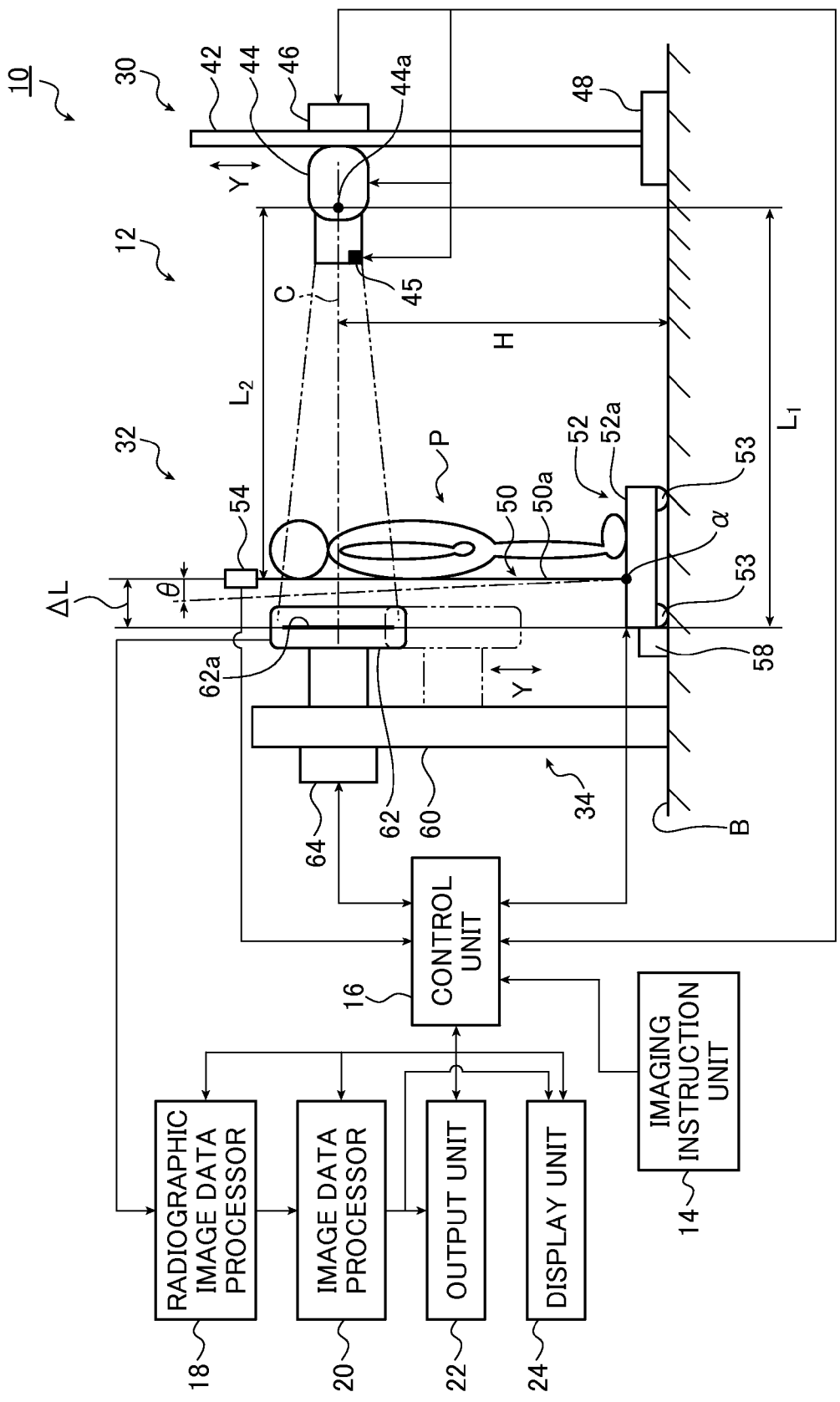
FIG. 1 is a schematic diagram illustrating a radiographic imaging system according to a first embodiment of the present invention.

FIG. 1 is a schematic diagram illustrating a radiographic imaging system according to a first embodiment of the present invention.

As shown in FIG. 1, a radiographic imaging system 10 (hereinafter, also referred to as an imaging system 10) includes an imaging unit 12, an imaging instruction unit 14, a control unit 16, a radiographic image data processor 18, an image data processor 20, an output unit 22, and a display unit 24.

The imaging instruction unit 14 sets an imaging menu, an imaging condition, an imaging mode, and the like and gives instructions for imaging a subject P. The imaging instruction unit 14 includes an input key (not shown) for setting an imaging menu, an imaging condition, and an imaging mode and an imaging instructor (not shown).

For example, a two-step push type imaging button is used as the imaging instructor. When the imaging button is pushed to a first step, for example, when the imaging button is half pushed, an imaging standby state is set. When the imaging button is pushed to a second step, for example, when the imaging button is fully pushed, imaging is started. The imaging instruction unit 14 outputs imaging information indicating the state where the imaging button is not pushed, the state where the imaging button is pushed to the first step, and the state where the imaging button is pushed to the second step through the use of displaying or outputting sound.

For example, as the imaging mode, three imaging modes are installed in the imaging system 10. The three imaging modes include a manual mode, an automatic mode and a long length mode. In the manual mode, imaging conditions such as radiation intensity, an irradiation time of radiation, and a dose of radiation of a radiation source 44 to be described later are manually set. In the automatic mode, imaging conditions such as the intensity of radiation and the irradiation time are set in advance. In the long length mode, a long length radiography that images a long length area is performed to acquire a long length image.

As described above, an imaging plane 62a of a typical radiation detector 62 has a size of about 42×42 cm. The long length radiography is an imaging method of continuously performing exposure plural times while causing an imaging area to move in the body axis direction, that is, in a long direction, of the subject P so as to capture a radiographic image of a long area greater than the imaging plane 62a of the radiation detector 62, such as the whole area of a spine (whole spine) or the whole area of legs (whole legs).

For example, in the long length radiography, the number of imaging times or the imaging positions are determined depending on the sizes of the imaging area and the imaging plane 62a of the radiation detector 62 and exposure (imaging) is continuously performed a number of times corresponding to the determined number of imaging times while causing the radiation detector 62 and the irradiation field of radiation, that is, the position of the radiation source 44, to move in the body axis direction. In the long length radiography, a radiographic image of a long area such as whole spine or the entirety of the whole legs is obtained by synthesizing plural radiographic images each acquired by a single exposure.

For convenience, it is assumed that an image obtained by a single exposure in the long length radiography, that is, a radiographic image obtained once by the radiation detector 62, is referred to as a short image and a normal imaging of capturing a radiographic image of the whole area of a subject by a single exposure is referred to as a general radiography operation. The manual mode and the automatic mode are modes in which the general radiography operation is performed.

Figure 2:
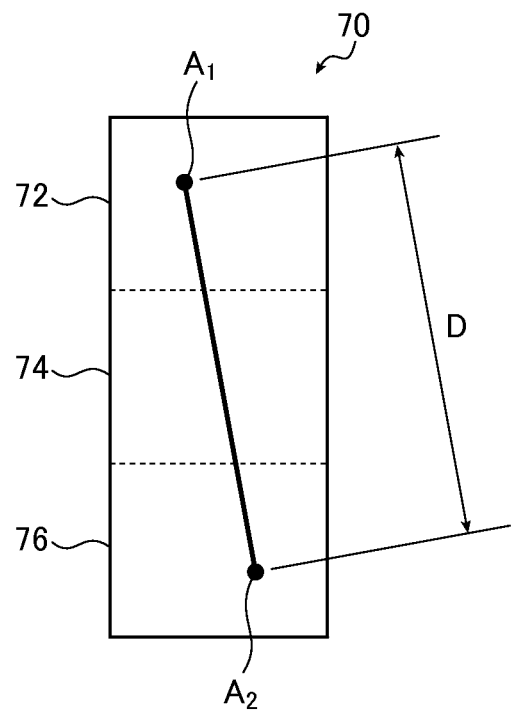
FIG. 2 is a schematic diagram illustrating a long image obtained by the radiographic imaging system according to the first embodiment of the present invention.

In this embodiment, a long image is obtained, for example, by three times of exposure and includes three short images 72, 74, and 76 like a long image 70 shown in FIG. 2.

In the long length mode of the imaging system 10, the capturing of a short image is continuously performed, that is, the movement of the radiation detector 62 and the irradiation field of radiation and the exposure at a predetermined interval are continuously performed, in the state where a radiographic engineer pushes the imaging button to the second step. The capturing of the short images, that is, the long length radiography, is ended when the pushing of the imaging button to the second step is released, that is, the imaging instruction is cancelled. By employing this configuration, the long length radiography can be rapidly stopped, for example, when the radiation engineer determines that an appropriate imaging operation cannot be performed because the subject P moves suddenly or the like.

However, the present invention is not limited to this configuration. For example, the number of imaging times, the position of the imaging area, the size of the imaging area, and the like may be set or input in advance and a predetermined number of short images may be automatically captured in response to an instruction to start the imaging.

The control unit 16 shown in FIG. 1 is a unit that controls the operation of each unit of the imaging system 10 in response to an imaging instruction signal or the like supplied from the imaging instruction unit 14.

The control unit 16 controls the imaging unit 12 to capture an image, for example, with set imaging menu, imaging condition, and imaging mode. The control unit 16 controls the radiographic image data processor 18 to read afterimage data of a previous radiographic image from the radiation detector 62 at a predetermined timing. The control unit 16 controls the image data processor 20 to perform a predetermined image process on the captured radiographic image data.

The control unit 16 controls the image data processor 20 to output a variety of image data such as a long image to the output unit 22 and the display unit 24 and controls the output unit 22 to output hard copies of various images such as a long image. The control unit 16 controls the display unit 24 to display various images such as a long image.

The imaging unit 12 includes an irradiation unit 30, a partition unit 32, and a radiation detecting unit 34.

The partition unit 32 is disposed adjacent to the radiation detecting unit 34. The irradiation unit 30 is disposed to face the radiation detecting unit 34 with the partition unit 32 interposed therebetween. That is, the irradiation unit 30 is disposed on the opposite side of the radiation detecting unit 34 in relation to the partition unit 32.

In the imaging unit 12, the distance between the radiation position 44a of the radiation source 44 to be described later in the irradiation unit 30 and the imaging plane 62a of the radiation detector 62 of the radiation detecting unit 34 is set to $L_1$.

The irradiation unit 30 radiates radiation to the radiation detector 62 to be described later of the radiation detecting unit 34. Radiation is radiated to a subject P from the irradiation unit 30 and the radiation transmitted through the subject P standing by the partition unit 32 is detected by the radiation detecting unit 34.

The irradiation unit 30 includes a guide rail 42, a radiation source 44, a distance measuring unit 45, and a source moving mechanism 46.

The radiation source 44 radiates radiation to the subject P and the radiation detector 62 and employs a radiation source typically used in radiographic imaging systems. Accordingly, although not shown, the radiation source 44 includes, for example, an X-ray tube, an X-ray movable aperture (collimator), an irradiation field lamp, a mirror, and the like.

The distance measuring unit 45 is disposed in the radiation source 44. The distance measuring unit 45 measures the distance to the plane 50a of the partition 50 of the partition unit 32 to be described later. The distance obtained by the distance measuring unit 45 is output to the control unit 16. Since the radiation position 44a of the radiation source 44 and position of the distance measuring unit 45, that is, a distance from the radiation position 44a of the X-ray tube to the distance measuring unit 45, is stored in advance in the control unit 16, the radiation position 44a of the radiation source 44, that is, the distance L2 from the radiation position 44a of the X-ray tube to the plane 50a of the partition 50 of the partition unit 32 to be described later, is obtained. The distance measuring unit 45 is of a non-contact type and for example, an ultrasonic range finder, a laser length measuring machine, or the like is used.

The distance L2 to the plane 50a of the partition 50 is used to calculate an enlargement ratio along with the distance L1 from the radiation position 44a of the radiation source 44 to the imaging plane 62a of the radiation detector 62. The enlargement ratio is calculated by the control unit 16, is output to the image data processor 20, and is used for image processes. The enlargement ratio is calculated as the enlargement ratio=L2/L1.

The radiation source 44 is supported by the guide rail 42. The guide rail 42 is disposed to extend in a predetermined direction corresponding to the body axis direction of a subject P (examinee) standing in the partition unit 32 to be described later, which is the direction perpendicular to the floor B in this embodiment, that is, the Y direction, and supports the radiation source 44 so as to be movable in the perpendicular direction. The guide rail 42 is disposed upright in the perpendicular direction, that is, the Y direction, from the pedestal 48.

The source moving mechanism 46 causes the radiation source 44 to move along the guide rail 42. The radiation source 44 can be made to move along the guide rail 42 and can be located at plural irradiation positions with different heights H, and the radiation source 44 can be fixed to a predetermined height H, through the use of the source moving mechanism 46. Accordingly, the irradiation field of radiation can be changed in the body axis direction of the subject P. Information of the height H of the radiation source 44 from the floor B can be obtained from the source moving mechanism 46. The information of the height H is output to the control unit 16.

The source moving mechanism 46 is not particularly limited and all moving units used in radiographic imaging systems imaging a long area can be used, such as a gear driving mechanism such as a rack-and-pinion gear, a screw driving mechanism, a ball-screw driving mechanism, a winding driving mechanism using a pulley or the like, and a mechanism using a cylinder such as an air cylinder or an oil cylinder.

The partition unit 32 includes a partition 50, a pedestal 52, and a tilt detecting unit 54. The partition unit 32 serves to determine the imaging position of a subject P in the optical axis C direction of the radiation source 44.

The partition 50 serves to locate the subject P at a predetermined position relative to the radiation detector 62 and is a radiation-transmitting panel member disposed upright from the pedestal 52 relative to the floor B. The partition 50 can be tilted about a connection portion α of the partition 50 and the pedestal 52. The partition 50 is disposed upright perpendicularly to the top surface 52a of the pedestal 52 in the state where a load is not applied thereto.

The pedestal 52 has the partition 50 disposed on the top surface 52a thereof and serves as a base onto which a subject P is loaded. Wheels 53 are disposed on the bottom of the pedestal 52. Accordingly, the partition unit 32 can be made to move. For example, a positioning member 58 positioning the partition unit 32 is disposed on the floor B. The partition unit 32 can be located at a predetermined position by bringing the pedestal 52 in contact with the positioning member 58.

The distance ΔL between the partition 50 and the imaging plane 62a of the radiation detector 62 can be approximately set to a predetermined distance through the use of the positioning member 58.

The tilt detecting unit 54 serves to detect the tilt θ of the partition 50 and is disposed, for example, on the top of the partition 50. The tilt θ of the partition 50 is an angle formed by the movement of the top of the partition 50 in the horizontal direction. For example, the movement of the partition 50 towards the radiation detector 62 is defined as forming a positive (+) angle and the movement of the partition 50 towards the radiation source 44 is defined as forming a negative (−) angle.

The tilt detecting unit 54 of the partition 50 is not particularly limited as long as it can detect the tilt θ of the partition 50, and for example, a tilt sensor or a gravity sensor can be used.

In this embodiment, the tilt θ of the partition 50 is detected by the use of the tilt detecting unit 54 and the detected tilt θ is output to the control unit 16. The value of the tilt θ is output to the image data processor 20 from the control unit 16 and is used for image correction such as trapezoidal distortion correction in the image data processor 20.

The control unit 16 may determine whether the tilt θ of the partition 50 is in an allowable range, and may output the value of the tilt θ of the partition 50 to the image data processor 20 when determining that the tilt exceeds the allowable range. In this case, when the tilt θ of the partition 50 is in the allowable range but the partition 50 is tilted, the image data processor 20 does not perform the image correction.

In this embodiment, regarding the allowable range of the tilt θ of the partition 50, for example, the movement of the top of the partition 50 in the horizontal direction is 8 mm with respect to 1200 mm. That is, the allowable tilt θ is θ=tan$^{-1}$(8/1200).

The radiation detecting unit 34 serves to detect radiation transmitted through a subject P and to obtain a radiographic image. The radiation detecting unit 34 includes an upright stand 60, a radiation detector 62, and a detector moving mechanism (detector moving unit) 64.

The radiation detector 62 is constructed, for example, by an FPD. The radiation detector 62 is a known radiographic detector, or radiographic image detector detecting radiation transmitted through a subject P, converting the detected radiation into an electrical signal, acquiring radiographic image data as analog data, and outputting the radiographic image data including the image of the subject P as analog data. The radiation detector 62 can employ both a direct-scheme FPD directly converting radiation into charges and an indirect-scheme FPD temporarily converting radiation into light and converting the light into an electrical signal.

The direct-scheme FPD includes a photoconductive film formed of amorphous selenium or the like, a capacitor, and a TFT as a switching element. For example, when radiation such as an X-ray is incident on the direct-scheme FPD, electron-hole pairs are generated from the photoconductive film. The electron-hole pairs are accumulated in the capacitor and the charges accumulated in the capacitor are read as an electrical signal through the use of the TFT.

On the other hand, the indirect-scheme FPD includes a scintillator layer formed of a fluorescent substance, a photo diode, a capacitor, and a TFT. The scintillator layer is formed of a fluorescent substance emitting light (fluorescing) in response to the incidence of radiation such as "CsI:Tl". The indirect-scheme FPD photoelectrically converts the light emitted from the scintillator layer in response to the incidence of radiation through the use of the photo diode and accumulates the converted charges in the capacitor, and the charges accumulated in the capacitor are read as an electrical signal through the use of the TFT.

The upright stand 60 serves to support the radiation detector 62 so as to be movable in the direction perpendicular to the floor B, that is, in the Y direction parallel to the moving direction of the radiation source 44. The upright stand 60 includes a guide rail (not shown) extending in the vertical direction (the Y direction) similarly to the guide rail 42 supporting the radiation source 44 and an engagement member (not shown) engaging with the guide rail so as to be movable in the Y direction and fixing the radiation detector 62.

The detector moving mechanism 64 can cause the radiation detector 62 to move in the Y direction similarly to the radiation source 44 and can position and stop the radiation detector 62 at plural imaging positions.

The detector moving mechanism 64 is not particularly limited and all moving units used in radiographic imaging systems imaging a long area can be used, such as a gear driving mechanism such as a rack-and-pinion gear, a screw driving mechanism, a ball-screw driving mechanism, a winding driving mechanism using a pulley or the like, and a mechanism using a cylinder such as an air cylinder or an oil cylinder, similarly to the source moving mechanism 46.

Accordingly, in the imaging system 10, the radiation source 44 and the radiation detector 62 can be made to move continuously or intermittently in the body axis direction of a subject P and thus it is possible to perform an imaging operation in the long length mode (long length radiography). Plural imaging positions of the radiation detector 62 preferably correspond to plural irradiation positions of the radiation source 44 in one to one.

The maximum imaging number of short images is not particularly limited and may be three or more. The imaging direction for the short images is not limited to the direction sequentially descending from the upside, but may be the direction sequentially ascending from the downside.

The imaging positions of the short images may be fixed, or may be arbitrarily changed, or may be any one thereof.

As described above, in the long length mode, the determined times of exposure, that is, plural times of imaging, are continuously performed while causing the radiation detector 62 and the irradiation field of radiation to move in the body axis direction of a subject P.

In the imaging system 10 according to this embodiment, for example, the imaging operation is performed at three stages of imaging positions in the long length mode. For this purpose, the position of the radiation detector 62 is made to intermittently move from up to down through the use of the detector moving mechanism 64 so as to sequentially stop at the imaging positions and the radiation source 44 is made to intermittently move through the use of the source moving mechanism 46 in synchronization with the radiation detector 62. When the movements of the radiation detector 62 and the radiation source 44 are intermittently stopped, a subject is exposed at the imaging positions, whereby the short images are captured.

That is, in the imaging system 10, it is possible to capture a long radiographic image from the top end of the first imaging position to the bottom end of the third imaging position, and it is possible to capture various long radiographic images such as the whole area of a spine (whole spine) or the whole area of legs (whole legs) by allowing a radiographic engineer capturing a radiographic image to arbitrarily select and determine the imaging positions and the times of imaging a short image depending on the imaging area of the subject P. In this way, by synthesizing the captured short images through the use of the image data processor 20 to be described later, a long radiographic image of whole spine or whole legs can be obtained.

Regarding the imaging positions, for example, two continuously imaging positions are made to partially overlap with each other. That is, the imaging area of the previously-captured image and the imaging area of the subsequently-captured image are made to overlap with each other. The overlapping area can be used as a connection criterion for synthesizing the images.

The radiographic image data processor 18 serves to perform processes such as an A/D (analog/digital) conversion process and a log conversion process on the output signal (image data of the radiographic image) read from the radiation detector 62 of the imaging unit 12 in response to an instruction from the control unit 16 and to convert the output signal into digital image data of the radiographic image. The radiographic image data processor 18 outputs the digital image data of the radiographic image having been subjected to the data processes to the image data processor 20.

The image data processor 20 performs image processes such as image correction and image synthesis on the processed digital image data acquired from the radiographic image data processor 18, converts the radiographic image data having been subjected to the image processes into monitor-displaying or printing-out data, and outputs the converted data to the output unit 22 and the display unit 24.

The image data processor 20 is embodied by a program (software) operating in a computer, or by dedicated hardware, or by a combination thereof.

The image data processor 20 serves to synthesize plural acquired short images to form a long radiographic image of a subject P when the imaging mode is the long length mode. When the image data processor 20 is supplied with plural short images as short digital image data, the digital image data are synthesized to generate radiographic image data indicating a long radiographic image of the subject P.

The image data processor 20 corrects the trapezoidal distortion of the short images on the basis of the value of the tilt θ output to the image data processor 20 from the control unit 16 and the information of the height H of the radiation source 44 when capturing an image.

Figure 3A:
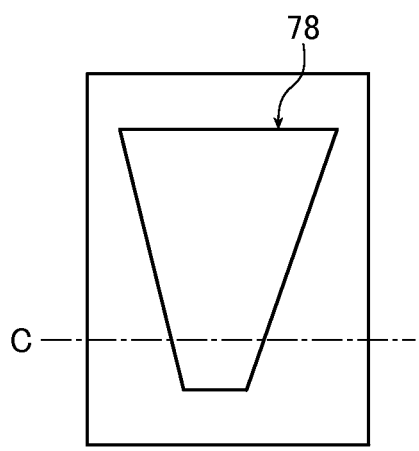
FIG. 3A is a schematic diagram illustrating a short image obtained by the radiographic imaging system according to the first embodiment of the present invention and FIG. 3B is a schematic diagram illustrating the corrected short image.
Figure 3B:
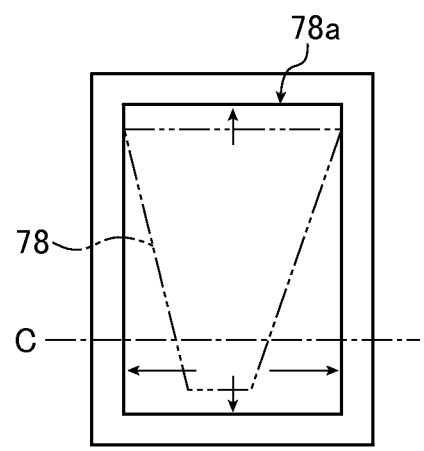

When a rectangular subject is imaged in the state where the partition 50 is tilted, a trapezoidal image 78 is obtained as shown in FIG. 3A. Accordingly, the trapezoidal distortion of the image 78 is corrected using the value of the tilt θ and the information of the height H of the radiation source 44 when capturing an image with respect to the position of the optical axis C of the radiation source 44, that is, the height H of the radiation source 44. As a result, the same rectangular image 78a as the imaged subject is obtained as shown in FIG. 3B.

The trapezoidal correction employs a known trapezoid correcting algorithm with respect to the position of the optical axis C of the radiation source 44, that is, the height H of the radiation source 44. An example of the trapezoid correcting algorithm is disclosed in JP 2010-94498 A.

The image data processor 20 corrects the deviation of the enlargement ratio using the enlargement ratio ($=L_2/L_1$) calculated by the control unit 16 and corrects the sizes in the digital image data to actual sizes. In the image correction using the enlargement ratio, for example, only the numerical value to which the size between two region of interest is corrected with reference to the enlargement ratio may be output or displayed without correcting the image. In this case, the numerical value may be output or displayed along with the values in the digital image data of the captured radiographic image.

The image data processor 20 can perform all the image processes which have been performed by various radiographic imaging systems, such as pixel defect correction, offset correction, dark correction, gain correction, shading correction, gradation correction, and density correction which are performed by calibration.

When the imaging mode is a mode corresponding to the general radiography and it is not necessary to perform the image synthesis, the image data processor 20 can perform the above-mentioned image processes other than the synthesis process on the digital image data of the radiographic image, can convert the processed image data into monitor-displaying data and printing-out data, and can output the converted data to the output unit 22 and the display unit 24.

The method of synthesizing short images to obtain a long image in the image data processor 20 is not particularly limited and all the known image synthesizing methods can be used.

For example, in the imaging system 10, since the imaging positions of the radiation detector 62, that is, the coordinate positions of the radiation detector 62, when capturing short images are known, a method of coupling/synthesizing the short images using the overlapping portions of the short images on the basis of the coordinate positions of the radiation detector 62 when capturing the short images can be used. Otherwise, a method of calculating image feature amounts of the overlapping portions, setting the portions having the same image feature amounts as edges of the images, and coupling the images at the edges to synthesize the images can be used.

The image data processor 20 can perform digital image processes such as gradation correction or density correction for matching densities or gradations on the digital image data of both partial images so as to match the overlapping portions of two continuously-captured adjacent partial images, which is performed to synthesize image data of plural partial images, can obtain image data of the partial images of which the overlapping portions are matched with each other, and can synthesize the partial images into a long image.

The output unit 22 outputs a hard copy using the printing-out data of the short images (partial images) or the long image (the whole image) output from the image data processor 20. The output unit 22 may output the image data of the partial images or the whole image output from the image data processor 20 to a network or a storage medium.

The display unit 24 displays the short images (partial images) or the long image (the whole image) using the monitor-displaying data of the short (partial) images or the long (whole) image output from the image data processor 20.

The display unit 24 may display selections or instructions which are necessary for the imaging operation through the use of a GUI and information such as a radiographic image or the number of imaging times may be displayed on a monitor.

In the imaging system 10 according to this embodiment, for example, when the floor B of a radiographic room is not flat but uneven and the partition 50 is tilted, the image correction is performed on the basis of the tilt $\theta$ of the partition 50 and the height of the radiation source 44 to correct the trapezoidal distortion and to correct the deviation of the enlargement ratio. Accordingly, it is possible to reduce an error in shape between a subject P and a captured short image and to obtain a short image of the subject P having a small error in relation to the actual size. Accordingly, regarding a long image finally obtained by synthesizing plural short images, it is possible to obtain a long image of a subject P having a small error in shape from the subject P and having a small error in relation to the actual size. As a result, it is possible to improve the diagnostic precision.

In the imaging system 10, for example, when a long image is obtained by three times of imaging, a long synthesized image 70 includes three short images 72 to 76 as shown in FIG. 2. At this time, the error between the actual distance and the distance D between a region of interest $A_1$ and a region of interest $A_2$ over three short images 72 to 76 in the long synthesized image 70 can be set to ±5 mm.

In the imaging system 10 according to this embodiment, since the image correction based on the tilt $\theta$ of the partition 50 can be performed, it is possible to make it unnecessary to adjust the position of the partition 50 and to adjust the tilt $\theta$ of the partition 50. Accordingly, it is possible to facilitate the work for installing the partition 50 and to simplify the configuration of the partition 50.

A long area imaging method in the imaging system 10 will be described below with reference to the flowchart shown in FIG. 4. In this embodiment, it is assumed that the whole area of a spine (whole spine) is imaged by three times of imaging to create a long image.

First, patient information of a patient as a subject P such as physical features such as height and weight, imaging sites, and imaging conditions are acquired (step S10).

In this case, a radiographic engineer sets the imaging menu such as imaging of whole legs and imaging of whole spine and the imaging mode in the radiographic imaging system 10 through the use of the imaging instruction unit 14 on the basis of the patient information. In this case, the long length mode is set as the imaging mode. An imaging start position of the long area imaging, that is, a first imaging position, is set through the use of the imaging instruction unit 14. The imaging conditions such as the exposure time and the radiation intensity are input. In this way, the imaging is prepared for.

As needed, an automatic long length mode or a preset automatic long length mode in which the imaging conditions are automatically set by the system or a manual long length mode in which a radiographic engineer can input/set the imaging conditions may be set in the long length mode through the use of the imaging instruction unit 14.

The partition 32 is made to move to bring the pedestal 52 in contact with the positioning member 58 and the partition 50 is located at a predetermined position in the front of the imaging plane 62a of the radiation detector 62 of the radiation detecting unit 34 (step S12).

The radiation source 44 of the irradiation unit 30 is made to move to an operating position (step S14). In this case, the radiation source 44 may be made to move to a predetermined position relative to an apparatus, for example, the imaging start position (the first imaging position) of the long area imaging, using an auto-positioning function.

Then, the tilt $\theta$ of the partition 50 is detected through the use of the tilt detecting unit 54 and the distance $L_2$ from the irradiation position (the radiation position 44a of the X-ray tube) of the radiation source 44 to the plane 50a of the partition 50 is measured through the use of the distance measuring unit 45 (step S16).

In step S16, the detected tilt $\theta$ of the partition 50 and the measured distance $L_2$ thereto are output to the control unit 16. The value of the tilt $\theta$ and the distance $L_2$ are output to the image data processor 20 from the control unit 16 and are used for the image correction to be described later.

As described above, after the tilt $\theta$ of the partition 50 and the distance $L_2$ to the partition 50 are acquired, a patient as a subject P is called in, the patient is made to stand on the pedestal 52 facing the radiation source 44, that is, so that the patient's back is against the plane 50a of the partition 50, the position of the subject P is determined, and then the imaging position of the subject P is determined (step S18).

An image of the subject is captured on the basis of the patient information acquired in step S10 (step S20). In this case, after one time of imaging is ended, for example, the radiation source 44 and the radiation detector 62 are made to synchronously move to a predetermined position from the head to the legs and three times of imaging in total are performed. For each imaging, image data is output from the radiation detector 62 to the radiographic image data processor 18, is converted into digital image data through the use of the radiographic image data processor 18, and is then output to the image data processor 20.

Three times of imaging in this embodiment will be described below in detail.

First, at the first time of imaging, when the imaging button of the imaging instruction unit 14 is pushed to the first step, the imaging unit 12 is in the standby state for the imaging under the control of the control unit 16.

When the imaging button is pushed to the second step, the first time of imaging is performed and radiation with a predetermined intensity is radiated from the radiation source 44 in the imaging unit 12 for a predetermined time. The radiated radiation is incident on the radiation detector 62 through the subject P and the radiation transmitted through the subject P is converted into an electrical signal (a radiographic image).

In the long length mode, details of the imaging timing, that is, the exposure timing, and the number of imaging times are output through sound or monitor display for each exposure for each time of imaging, so as to be recognized by the radiographic engineer performing an imaging operation.

The radiographic image data processor 18 reads the captured radiographic image from the radiation detector 62 after a predetermined accumulation time passes, performs processes such as the A/D conversion, and supplies the resultant to the image data processor 20. The image data processor 20 acquires the radiographic image supplied from the radiographic image data processor 18 and stores the radiographic image acquired in the first time of imaging as a first short image at the first imaging position.

The image data processor 20 may supply the first short image to the display unit 24 so as to cause the display unit 24 to display the first short image as a preview image before synthesis.

The radiographic engineer can confirm any defect in the captured radiographic image, for example, can check whether the subject P moves from the imaging range, through the use of the preview image displayed by the display unit 24. Accordingly, when it is intended to stop the imaging due to the defect, it is possible to stop the imaging.

When the first time of imaging is ended, the radiation detector 62 is made to move to a second imaging position through the use of the detector moving mechanism 64 and the radiation source 44 is made to move to a second imaging position through the use of the source moving mechanism 46 at the same time.

After the radiation detector 62 and the radiation source 44 move to the second imaging position, the second time of imaging is started. Similarly to the first time of imaging, in the imaging unit 12, radiation with a predetermined intensity is radiated from the radiation source 44 for a predetermined time, the radiated radiation is incident on the radiation detector 62 through the subject P, the radiation transmitted through the subject P is converted into an electrical signal, and a radiographic image can be thus obtained.

The radiographic image data processor 18 reads the radiographic image captured at the imaging position N=2 from the radiation detector 62 after a predetermined accumulation time passes, performs processes such as the A/D conversion, and supplies the resultant to the image data processor 20. The image data processor 20 stores the radiographic image (short image) supplied from the radiographic image data processor 18 as a second short image at the second imaging position, that is, as a radiographic image acquired in the second time of imaging.

The second short image is supplied to the display unit 24 so as to display the second short image as a preview image, similarly to the first short image.

When the second time of imaging is ended, the radiation detector 62 and the radiation source 44 are made to move to a third imaging position, similarly to the second time of imaging.

After the radiation detector 62 and the radiation source 44 move to the third imaging position, the third time of imaging is started. Similarly to the second time of imaging, in the imaging unit 12, the radiation radiated from the radiation source 44 and transmitted through the subject P is converted into an electrical signal (radiographic image) by the radiation detector 62. The radiographic image data processor 18 reads data of the radiographic image from the radiation detector 62, performs processes such as the A/D conversion thereon, and supplies the resultant to the image data processor 20. The image data processor 20 stores the radiographic image supplied from the radiographic image data processor 18 as a third short image at the third imaging position, that is, as a radiographic image acquired in the third time of imaging.

The third short image is supplied to the display unit 24 so as to display the third short image as a preview image, similarly to the first short image.

After the third time of imaging is ended, the image data processor 20 performs the above-mentioned imaging processes of the image data processor 20, such as image processes based on the tilt $\theta$ and the distance $L_2$, on the digital image data of three captured short images, and then synthesizes three short images to obtain digital image data of a long image (step S22).

The digital image data of the long image is output to the output unit 22 and a hard copy is created by the output unit 22 (step S24). The digital image data of the long image is output to the display unit 24 and the long image is displayed by the display unit 24 (step S24). In this way, it is possible to obtain a long diagnostic image. The obtained diagnostic image is used to diagnose the patient (the subject P) (step S26).

In the imaging system 10, the general radiography other than the long area imaging can be performed similarly to the known radiographic imaging systems, and may be performed with the tilt of the partition 50 in the allowable range, similarly to the long area imaging.

In the imaging method according to this embodiment, in step S16, when the partition 50 is tilted, the value of the tilt $\theta$ is output to the image data processor 20 for the image correction, but the present invention is not limited to this configuration. For example, in step S16, it may be determined by the control unit 16 whether the value of the tilt $\theta$ is in a predetermined allowable range, and the value of the tilt $\theta$ may not be output to the image data processor 20 so as not to perform the image correction in the image data processor 20 when it is determined that the value of the tilt $\theta$ is in the allowable range.

When the subject P is loaded onto the pedestal 52, the weight thereof may be applied to the partition 50. Accordingly, after the subject P is located onto the pedestal 52, the tilt $\theta$ of the partition 50 may be measured again, the value of the tilt $\theta$ of the partition 50 acquired again by this measurement may be output to the image data processor 20, and the value of the tilt may be used for the image correction.

In the imaging method according to this embodiment, before the subject P is loaded onto the pedestal 52, the tilt $\theta$ of the partition 50 is measured and the distance $L_2$ to the partition 50 is measured, but the present invention is not limited to this configuration. For example, after the subject P is loaded onto the pedestal 52 and the image thereof is captured, the tilt $\theta$ of the partition 50 and the distance $L_2$ to the partition 50 may be measured. In this case, the measured value of the tilt $\theta$ and the distance $L_2$ are output to the control unit 16 and the value of the tilt $\theta$ and the distance $L_2$ thereto are used for the image correction in the image data processor 20.

A second embodiment of the invention will be described below.

Figure 5:
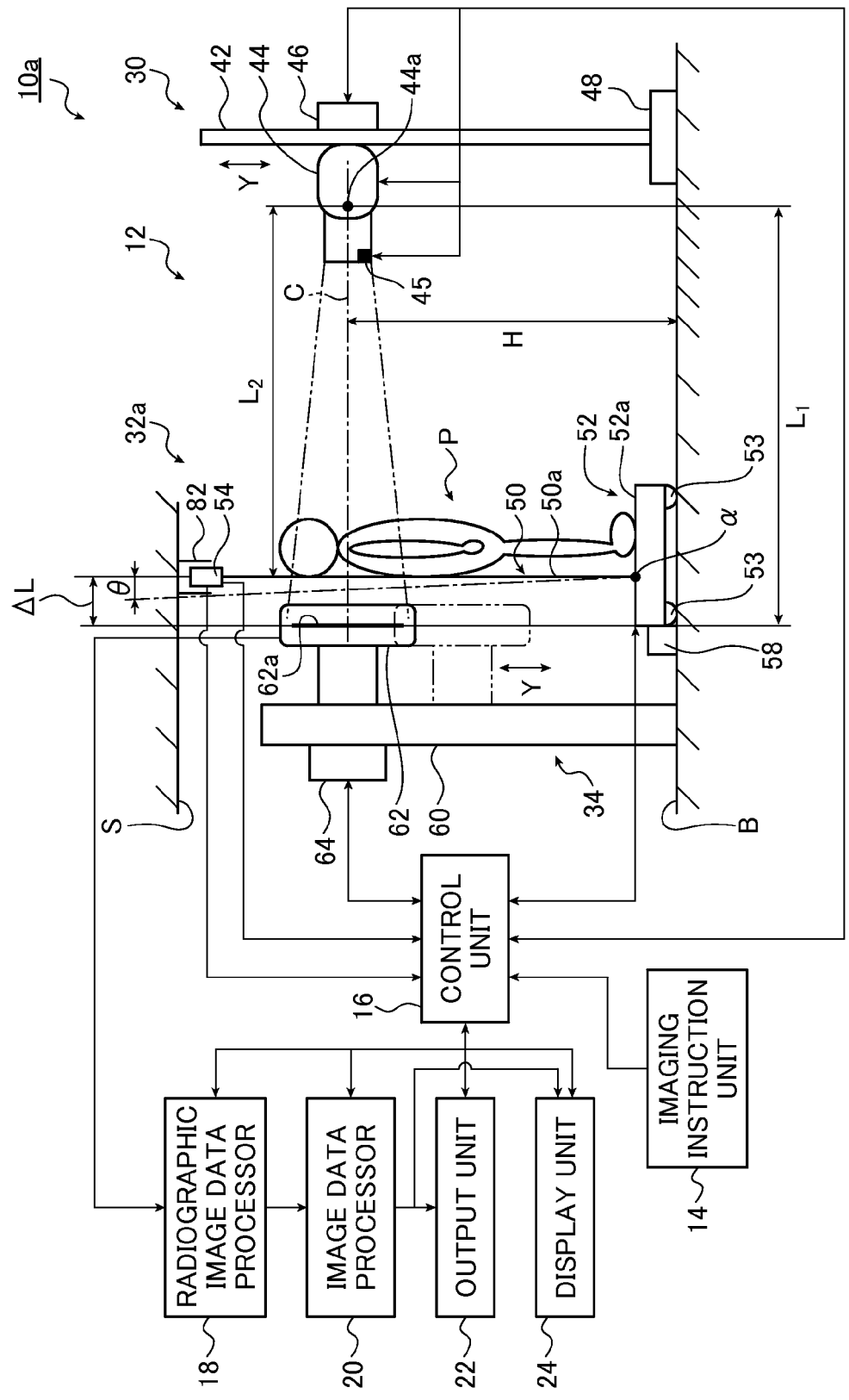
FIG. 5 is a schematic diagram illustrating a radiographic imaging system according to a second embodiment of the present invention.

FIG. 5 is a schematic diagram illustrating a radiographic imaging system according to a second embodiment of the invention.

In this embodiment, the same elements as the radiographic imaging system 10 according to the first embodiment shown in FIG. 1 are referenced by the same reference signs and the detailed description thereof will not be repeated.

A radiographic imaging system 10a (hereinafter, also referred to as an imaging system 10a) according to this embodiment shown in FIG. 5 is different from the radiographic imaging system 10 (see FIG. 1) according to the first embodiment in the configuration of the partition unit 32a and is equal to the radiographic imaging system 10 according to the first embodiment in the other configurations, the detailed description of which will not be repeated.

The partition unit 32a of the imaging system 10a according to this embodiment is different from the partition unit 32 of the first embodiment in the direction of the wheels 53 installed in the pedestal 52. The rotation axis of the wheels 53 is perpendicular to the plane 50a of the partition 50. A guide 82 is installed on the ceiling S. The tilt detecting unit 54 is disposed on the top of the partition 50. The top of the partition 50 is inserted into the guide 82 and the partition 50 moves in the direction parallel to the plane 50a of the partition 50 in this state.

In this embodiment, similarly to the imaging system 10 according to the first embodiment, the tilt of the partition 50 is detected through the use of the tilt detecting unit 54, and the image correction is performed on the basis of the tilt θ of the partition 50 to correct the trapezoidal distortion or the like and to correct the deviation of the enlargement ratio. Accordingly, for example, when the floor B is not flat but uneven and the partition 50 is thus tilted, it is possible to reduce the error in shape from a subject P and to obtain a short image of the subject P having a small error in relation to the actual size. Accordingly, regarding a long image finally obtained by synthesizing plural short images, it is possible to obtain a long image of the subject P having a small error in shape from the subject P and having a small error in relation to the actual size. As a result, the error between the actual distance and the distance D between two regions of interest $A_1$ and $A_2$ over plural short images 72 to 76 in the long synthesized image 70 shown in FIG. 2 can be set to ±5 mm.

In this embodiment, since the image correction can be performed on the basis of the tilt θ of the partition 50, it is possible to make it unnecessary to adjust the position of the partition 50 and to adjust the tilt θ of the partition 50. Accordingly, it is possible to facilitate the work of installing the partition 50.

In this embodiment, it may be determined by the control unit 16 whether the value of the tilt θ of the partition 50 is in an allowable range, and the image data processor 20 may be made to perform the image processes, similarly to the imaging system 10 according to the first embodiment, when it is determined that the value of the tilt exceeds the allowable range.

Both the above-mentioned imaging systems 10 and 10a according to the embodiments have been applied to the radiographic imaging system for imaging a subject P with an upright position, but the present invention is not limited to this configuration. The present invention may be applied to a radiographic imaging system for imaging a subject P with a recumbent position.

It has been stated in any of the above-mentioned imaging systems 10 and 10a according to the embodiments that the irradiation field of radiation in the long area imaging is changed by causing the radiation source 44 to move in the body axis direction of the subject P (the Y direction), but the present invention is not limited to this configuration. In the present invention, various known units changing the irradiation field of radiation can be used.

For example, the unit changing the irradiation field of radiation may employ a method of changing the irradiation field of radiation by changing the angle of the radiation source, that is, by so-called rotating the tube. A method of changing the irradiation field of radiation by employing an X-ray tube that can irradiate the whole area of the long area imaging with an X ray as a radiation source and an aperture that regulates the irradiation field of an X ray from the X-ray tube and causing the aperture to move in the body axis direction can be also employed by the unit changing the irradiation field of radiation.

An X-ray tube suspending machine supporting an X-ray source, causing the X-ray source to move in the horizontal direction through the use of a horizontal driving unit traveling on the ceiling, and causing the X-ray source to move in the vertical direction through the use of a vertical driving unit may be employed. In this case, the irradiation direction of an X ray is controlled by rotationally driving the X-ray source through the use of a rotational driving unit.

The present invention basically has the above-mentioned configuration. While the radiographic imaging system and the radiographic imaging method according to the present invention have been described above in detail, the present invention is not limited to the embodiments, but may be improved or modified in various forms without departing from the concept of the present invention.

What is claimed is:

1. A radiographic imaging system capturing a radiographic image of a subject, comprising:
    a radiation detector that detects radiation from which the radiographic image is obtained;
    a radiation source that irradiates the radiation detector with the radiation;
    a partition that is disposed adjacent to the radiation detector and that locates the subject at a predetermined position relative to the radiation detector;
    a distance measuring unit that measures a distance between the partition and the radiation source;
    a tilt detecting unit that measures a tilt of the partition; and
    an image processor that corrects the captured radiographic image based on the distance between the partition and the radiation source obtained by the distance measuring unit and the tilt of the partition obtained by the tilt detecting unit.

2. The radiographic imaging system according to claim 1, wherein the distance measurement unit measures a distance between the partition and the radiation source before or after a radiographic image is obtained.

3. The radiographic imaging system according to claim 2, wherein the tilt detecting unit measures a tilt of the partition during capturing a radiographic image.

4. The radiographic imaging system according to claim 2, further comprising a detector moving unit that causes the radiation detector to move in the length direction of the subject,
    wherein the image processor synthesizes a plurality of images, which are obtained by causing the radiation detector to move in the length direction of the subject through the use of the detector moving unit, irradiating the subject with radiation from the radiation source, and capturing the images of the subject divided in the length direction, and creates a long radiographic image.

5. The radiographic imaging system according to claim 4, wherein two subsequent imaging positions are made to partially overlap with each other when capturing the images of the subject divided in the length direction and the image processor matches the overlapping portions to create the long radiographic image.

6. The radiographic imaging system according to claim 1, wherein the tilt detecting unit measures a tilt of the partition during capturing a radiographic image.

7. The radiographic imaging system according to claim 6, further comprising a detector moving unit that causes the radiation detector to move in the length direction of the subject,
    wherein the image processor synthesizes a plurality of images, which are obtained by causing the radiation detector to move in the length direction of the subject through the use of the detector moving unit, irradiating the subject with radiation from the radiation source, and capturing the images of the subject divided in the length direction, and creates a long radiographic image.

8. The radiographic imaging system according to claim 7, wherein two subsequent imaging positions are made to partially overlap with each other when capturing the images of the subject divided in the length direction and the image processor matches the overlapping portions to create the long radiographic image.

9. The radiographic imaging system according to claim 1, further comprising a detector moving unit that causes the radiation detector to move in the length direction of the subject, wherein the image processor synthesizes a plurality of images, which are obtained by causing the radiation detector to move in the length direction of the subject through the use of the detector moving unit, irradiating the subject with radiation from the radiation source, and capturing the images of the subject divided in the length direction, and creates a long radiographic image.

10. The radiographic imaging system according to claim 9, wherein two subsequent imaging positions are made to partially overlap with each other when capturing the images of the subject divided in the length direction and the image processor matches the overlapping portions to create the long radiographic image.

11. A radiographic imaging method of capturing a radiographic image of a subject by the use of a radiation detector, a partition that locates the subject at a predetermined position relative to the radiation detector, and a radiation source that irradiates the radiation detector with radiation, the radiographic imaging method comprising the steps of:

measuring a distance between the partition and the radiation source and a tilt of the partition;

capturing the radiographic image of the subject; and correcting the captured radiographic image based on the distance between the partition and the radiation source and the tilt of the partition.

12. The radiographic imaging method according to claim 11, wherein capturing the radiographic image of the subject comprising measuring a second tilt of the partition; and wherein correcting the captured radiographic image comprising correcting the captured radiographic image based on the second tilt of the partition.

13. The radiographic imaging method according to claim 12, wherein the step of capturing the radiographic image of the subject includes:

a step of causing the radiation detector to move in the length direction of the subject, irradiating the subject with the radiation from the radiation source, and capturing a plurality of images of the subject divided in the length direction; and a step of synthesizing the plurality of images obtained by imaging the subject divided in the length direction to create a long radiographic image.

14. The radiographic imaging method according to claim 13, wherein when capturing the images of the subject divided in the length direction, two subsequent imaging positions are made to partially overlap with each other to image the subject divided in the length direction and the overlapping portions are matched with each other to create the long radiographic image.

15. The radiographic imaging method according to claim 11, wherein the step of capturing the radiographic image of the subject includes:

moving the radiation detector in the length direction of the subject, irradiating the subject with the radiation from the radiation source, and capturing a plurality of images of the subject divided in the length direction; and synthesizing the plurality of images obtained by imaging the subject divided in the length direction to create a long radiographic image.

16. The radiographic imaging method according to claim 15, wherein when capturing the plurality of images of the subject divided in the length direction, two subsequent imaging positions are made to partially overlap with each other to image the subject divided in the length direction and the overlapping portions are matched with each other to create the long radiographic image.

* * * * *